United States Patent [19]

Lee

[11] Patent Number: 5,306,305
[45] Date of Patent: Apr. 26, 1994

[54] METHODS OF COATING IMPLANTS WITH BONY STRUCTURE

[75] Inventor: Dosuk Lee, Brookline, Mass.

[73] Assignee: Etex Corporation, Cambridge, Mass.

[21] Appl. No.: 830,174

[22] Filed: Jan. 31, 1992

[51] Int. Cl.$^5$ .............................................. A61F 2/54
[52] U.S. Cl. .................................... 623/16; 435/177; 435/240.23
[58] Field of Search ................ 435/290.2, 290.23, 177, 435/182; 623/16, 66

[56] References Cited

U.S. PATENT DOCUMENTS

| | | | |
|---|---|---|---|
| 4,282,317 | 8/1981 | Roth | 435/240.2 |
| 4,999,297 | 3/1991 | Minoura et al. | 435/240.23 |
| 5,197,985 | 3/1993 | Caplan et al. | 623/16 |

OTHER PUBLICATIONS

L. Gerstenfeld et al. (1987) Dev. Biology 122:49–60 Expression of Differentiated Function by Mineralizing Cultures of Chicken Osteoblasts.
M. Finer, et al. (1985) Mo. Cell. Bio. 5:1415–1424, Collagen Expression in Embryonic Chicken Chondrocytes Treated with Phorbol Myristate Acetate.
Wong and Cohen (1975) P.N.A.S. 72:3167–3171, Target Cells in Bone for Parahormone and Calcitonin are Different: Enrichment for Each Cell Type by Sequential Digestion of Mouse Calvaria.
U. Bhargava, et al. 91988) Bone 9:155–163, Ultrastructural Analysis of Bone Nodules Formed in Vitro by Isolated Fetal RAt Calvaria Cells.
B. Ecarot-Charrier, et al. (1988) Bone 9:147–154, Mineralization in Osteoclast Cultures: a Light and Electron Microscopic Study.
C. Bellows, et al. (1986) Calc. Tiss. Int. 38:143–154, Mineralized Bone Nodules Formed in Vitro from Enzymatically Released Rat Calvaria Cell Populations.
Tenenbaum and Heersche (1982) Calc. Tiss. Int. 34:76–79, Differentiation of Osteoclasts and Formation of Mineralized Bone In Vitro.
P. Nijweide, et al. (1982) J.C.B. 93:318–323, Bone Formation and Calcification by isolated Osteoblastlike Cells.
K. Yoon, et al. (1987) Bio. Biophys. Res. Comm. 148:1129–1136, Tissue Specificity and Developmental Expression of Rat Osteopontin.
R. Umansky (1966) Dev. Bio. 13:31–56, The Effect of Cell Population Density on the Developmental Fate of Reaggregating Mouse Limb Bud Mesenchyme.
M. Urist, et al. 91983) Science 220:680–686, Bone Cell Differentiation and Growth Factors.
Osdoby and Caplan (1979) Dev. Bio. 73:84–102, Osteogenesis in Cultures of Limb Meenchymal Cells.
H. Sudo, et al. (1983) J.C.B. 96:191–198, In Vitro Differentiation and Calcification in a New Clonal Osteogenic Cell Line Derived from Newborn Mouse Calvaria.
B. Ecarot-Charrier, et al. (1983) J.C.B. 96:639–643, Osteoblasts Isolated from Mouse Calvaria Initiate Matrix Mineralization in Culture.
Wuthier and Register (1985) in The Chemistry and Biology of Mineralized Tissues, ed. W. T. Butler pp. 113–124, Role of Alkaline Phosphatase, a Polyfunctional Enzyme, in Mineralizing Tissues.
M. Karnovsky (1971) Am. Soc. Cell. Bio. Abstract 284, p. 146, Use of Ferrocyanide-Reduced Osmium Tetroxide in Electron Microscopy.

(List continued on next page.)

*Primary Examiner*—David Isabella
*Assistant Examiner*—Debra S. Brittingham
*Attorney, Agent, or Firm*—Bertram I. Rowland

[57] ABSTRACT

Implants associated with bone are coated with natural bony tissue by incubating the implant with osteoblasts under conditions where the osteoblasts grow and lay down a bony coating. Different methods are provided for maintaining the osteoblasts in contact with the implant and allowing for the growth and maintenance of the osteoblasts with formation of the bony tissue. The resulting coated implants can provide for a better juncture with the natural tissue in the patient, so as to provide for a more comfortable and effective prosthesis or other device.

6 Claims, 5 Drawing Sheets

OTHER PUBLICATIONS

Y. Gotoh, et al. (1990) Bio. Biophys. Res. Comm. 173:471–479, Comparison of Two Phosphoproteins in Chicken Bone and Their Similarities to the Mammalian Bone Proteins, Osteopontin and Bone Sialoprotein II.

Y. Gotoh, et al. (1990) Eur. J. Biochem. 187:49–58, Ientification and Characterization of the Major Chicken Bone Phosphoprotein.

M. Moore, et al. (1991) Biochemistry 30:2501–2508, Characterization of a cDNA For Chicken Osteopontin: Expression During Bone Development, Osteoblast Differentiation, and Tissue Distribution.

L. Gerstenfeld, et al. (1990) The Anatomical Record 228:93–103, Expression and Ultrastructural Immunolocalization of a Major 66 kDa Phosphoprotein Synthesized by Chicken Osteoblasts During Mineralization In Vitro.

L. Gerstenfeld, et al. (1987) Dev. Biology 122:49–60, Expression of Differentiated Function by Mineralizing Cultures of Chicken Osteoblasts.

METHODS OF COATING IMPLANTS WITH BONY STRUCTURE

INTRODUCTION

1. Technical Field

The field of the subject invention concerns the coating of structures for in vivo implantation with bony structure.

BACKGROUND

Bone-calcified tissue is a highly complex and dynamic organ in the human body. Regulated chemical components within the bone-forming cells control the extracellular chemical activities which produce the calcified bone materials Escarot-Charrier, et al., *J. Cell. Biol.* (1983), 96, 639-643; Sudo, et al., J. Cell. Biol. (1983), 96, 191-198; Stein et al., *Proc. Natl. Acad. Sci. USA* (1988)). The two primary chemical components of bone are inorganic calcium phosphate solids and organic collagen matrix. Several different types of calcium phosphate minerals exist, including calcium hydroxyapatite, tricalcium phosphate, octacalcium phosphate, etc. Only calcium hydroxyapatite has been established as a major mineral constituent in human bone. The size of the hydroxyapatite crystals found in bone are extremely small, on the order of several hundred Å wide and several microns long. These tiny crystals lend their unique characteristics to the rigidity of the bone tissue.

Collagen is a ductile organic bio-polymer that provides molecular binding sites for the calcium phosphate minerals and provides the flexibility to the overall mechanical property of the bone. Collagen is a major protein component in the human body and is found in skin, cartilage and tendon.

It is the combination of the calcium phosphate minerals and the collagen, in combination with other minor components, which provides the unique structural, chemical and biological properties of bone tissue.

For the most part, bone or bony implants involve non-biological materials, primarily metal alloys, such as titanium alloys, stainless steel and cobalt chromium alloys. These materials provide for superior mechanical properties, such as fracture toughness, load properties and ability to maintain a good stress-strain relationship. Their use is predicated on the inability to produce bony structures which can be successfully introduced to replace diseased, fractured or otherwise non-functional bony structure present in the host.

Greater than fifty percent of the total orthopaedic surgery performed on patients today fails during the first ten years. The failure is primarily due to the lack of biocompatibility between the prosthetic material and the naturally occurring bone tissue. The inability for bony tissue to provide a strong bond with the prosthetic device causes several clinical complications. The most serious complication is a tissue rejection process that occurs along the surface of the prosthetic material which results in bone resorption. The bone resorption process creates a "gap" between the prosthesis and the adjacent bone surface. This gap facilitates the movement of the prosthesis, causing severe pain to the post-operative patient and the ultimate failure of the implant.

Despite the large amount of effort which has already been expended in trying to solve this problem, the problem has remained substantially intractable. Efforts have been primarily directed to using new methods of coating orthopaedic prostheses with calcium phosphate minerals. There has been continued concern about a natural integration between new bone growth and the prosthesis. There is, therefore, substantial interest in finding new techniques which will enhance the integration between new bone growth and prostheses and provide for extended useful periods without the problems associated with prostheses today.

SUMMARY OF THE INVENTION

Methods and devices are provided relating to dental and orthopaedic implants, where prostheses are coated with natural tissue using viable bone-forming osteoblastic cells. The cells are grown in a medium capable of providing for a stable coating of a prosthesis, so as to form bony tissue coating on the prosthesis. After implantation of the prosthesis, the cells, if present, provide for the continuous growth of the bony tissue and integration with the native bony tissue of the patient.

DESCRIPTION OF THE SPECIFIC EMBODIMENTS

Methods and devices are provided for use as implants for dental and orthopaedic applications. The implants comprise a device of other than a naturally occurring tissue, usually metal or metal alloy, coated with bony tissue, as a result of growth of osteoblast cells on the device. The patient's own cells continue to grow and may be present as viable cells upon introduction of the implant into the patient.

The subject methods and devices may be used with a wide variety of devices, particularly dental and orthopaedic implants, such as prostheses for the hip, joints, partial bone replacements of tibia, femur, and partial and full denture fixtures. A wide variety of metal alloy prostheses are available, which are made for the most part of metal alloys, such as titanium alloys, stainless steel and cobalt chromium alloys. These prostheses may have areas, particularly those areas which are to be associated with the native bony tissue, which are porous. The porosity may be as a result of the use of beads which are tightly held together, but allow for channels between the beads for bony ingrowth. Other metal implant devices may include textured surfaces to increase the surface area.

The osteoblast cells may be autologous, allogeneic, xenogeneic, or may be modified cells as a result of recombinant technology (Osdoby and Caplan, *Dev. Biol.*

(1979), 73, 84-102; Urist, et al., *Science* (1983), 220, 680-686; Urmansky et al., *Dev. Biol.* (1966), 13, 13-56; Yoon, et al., *Biochem. Biophys. Res. Comm.* (1987), 148, 1129-1136). Thus, the cells may be modified by diminishing or inhibiting the production of major histocompatibility antigens, Class I and/or Class II or members thereof, e.g. mls. Preferably, the cells will be autologous and may be obtained from the patient bone, such as tibia, femure, ulna, humerus and ilium. Usually, tissue of a size of about 0.5 to 3 mm$^3$ is obtained using sterile surgical syringe or other equipment for extracting the bone tissue (Nijweidi, et al., *J. Cell Biol.* (1982), 93, 318-323; Tenenbaum and Heersche, *Calcif Tissue Int.* (1982), 33, 76-79; Bellows, et al., *Calcif. Tissue Int.* (1986), 38, 143-154). Once the tissue has been isolated, it may then be processed.

The tissue fragments are washed in a sterilized solution, normally comprising only inorganic salts and antibiotics. The salts include alkali metal phosphates, e.g. sodium phosphate, sodium chloride, potassium chloride, potassium phosphate, etc (Gerstenfield, et al., *Developmental Biology* (1987), 122, 49-60). The total concentration of the salts will generally be in the range of about 130 to 150 mM. The antibiotics may include penicillin, streptomycin, or combination thereof, generally at a concentration which will maintain the sterile nature of the medium. These concentrations are conventional and need not be indicated here. The pH of the solution will generally be in the range of about 6.5 to 8, preferably about 7 to 7.5.

Thin layers of tissue comprising osteoblast cells are provided from the original fragments and carefully washed in sterilized solutions, the solutions having been described above. The tissue is then enzymatically treated in a proteolytic medium, conveniently comprising trypsin-collagenase. The concentration of the enzymes will generally be in the range of about 2% to 3%.

The solution for the proteolysis will be as recommended by the supplier, generally comprising phosphate buffer solution (PBS). The resulting individual cells are then cold-filtered (0.45 μm) to remove the protein solution and any non-osteoblastic components. The cells are then repeatedly dispersed in fresh media and filtered, the process being repeated about three to five times and may require up to about two to twelve hours. The medium employed may be MEM (minimum essential medium, containing 5-15, usually 10%, serum e.g. fetal bovine serum (FBS), or human serum). The final filter-passage employs a 0.2 μm filter.

The cells are then dispersed in buffer solution comprising PBS+MEM+FBS and then cold centrifuged and the pellet dispersed in a dilute gel solution comprising a growth medium, e.g. MEM media with 0 to 15% fetal bovine serum and from about 0.1 to less than about 1% of a proteinaceous gelling agent, preferably about 0.5% (Wuthier and Register (1985), In: *The Chemistry and Biology of Mineralized Tissues* (W. T. Butler eds.), Ebsco Media, Inc., Birmingham, AL, pp. 113-124). The gelling agent may be any physiologically acceptable, compatible gelling agent, such as collagen, agar, gelatin. Generally, the cells will be present at a concentration of about $1.0 \times 10^5$ to $5.0 \times 10^5$ cells/ml, more usually 2 to $3 \times 10^5$ cells/ml.

The cells are expanded by growing the cells over a period of about 1-4 weeks, preferably about 2-3 weeks, maintaining the cells in the growth medium at about 37° C. with 5% carbon dioxide. The solution is changed frequently, generally not more than about every day, and usually not less than about every fourth day, preferably about every two days. During this period, the cells will have been expanded from about 100 to 1000 fold.

Any of a variety of growth media may be employed, referred to as complex growth media, with a media providing an environment similar to that of natural fluids, cellular or extracellular. Typically, the media will include a source of amino acids, inorganic salts, a source of metabolic energy, normally metabolizable or assimilable saccharide source, e.g. glucose, and preferably a source of growth factors, e.g. fetal bovine serum. In addition, vitamins, proteinaceous compositions as a source of amino acids, and carbonate will also be present. In order to protect the medium from contamination, antibiotics and antimucotics may be employed. Inorganic salts will also be present, which approximate the natural medium. Conventional media which may be employed include sodium biocarbonate, penicillinstreptomycin solution, β-butyl-parahydroxybenzoate (antimycotic) (150-250 μg/ml).

The cells are now ready to be coated on the implant surface. The cells are dispersed in a growth medium as described above, where the medium contains a sufficient amount of gelling agent to allow for maintenance of a coating on the implant device. Usually, from about 1 to 5 weight percent of the gelling agent will suffice to provide the necessary thickness and coating properties. The concentration of cells will generally be in the range of about $1 \times 10^5$ to $10 \times 10^5$ cells/75cm$^2$, more usually 5 to $7 \times 10^5$ cells/75cm$^2$. A portion or all of the implant to be coated may be immersed in the medium, preferably only that portion to be coated. Areas exposed to the medium, which are not to be coated, may be wiped or the medium otherwise removed. Alternatively, the device may be covered with tape or other protective removable coating to prevent contact of areas to remain uncoated with the medium. The device will be maintained in the medium for a time in the range of about 1 sec to 10 min, the particular time not being critical, so long as it is sufficient to insure that the particular surface is completely covered with gel material containing bone cells.

The implants may then be removed from the solution insuring that a thin layer, 0.05-1 mm, usually about 0.1-0.5 mm of the gel media containing the osteoblasts is maintained on the device surface. The devices are then placed in a medium which supports growth, usually an environment at about 37° C. and 5% carbon dioxide for 1 hr-24 hrs. The implants are kept in a sterile chamber (FIG. 4A) containing a growth medium, e.g. MEM medium+serum (~10%).

The implants are then incubated for at least about 15 days, usually about 21 days, and not more than about 30 days (Lian, et al., *Calcif. Tissue Int.* (1982), 34, 582-887). The conditions for the incubation are: 37° C. and 5% carbon dioxide. At approximately the 21st day, the medium is exchanged and medium containing 0.1 M β-glycerol phosphate growth media (Sigma), 10% FBS, 0.25 mg/ml ascorbic acid replaces the MEM media described above. Then, under the same conditions (37° C. and 5% CO$_2$) implants are incubated for an additional 1-2 weeks.

During the period of incubation, the cells multiply and proliferate along the palisade of the implant surface. The osteoblastic cells are physically held to the surface by the gel. Upon coating of the device, which may include total encapsulation of the implant by the cells, bony material is laid down.

The subject methodology allows for extended periods of growth, generally being sixty days or more. The gel medium serves a plurality of purposes. It allows the components required for the growth and maintenance of the osteoblastic cells to diffuse through the gel and the 0.2 μm filter provided by the sterile chamber device, as well as allowing for removal of waste products from the gel medium. The gel provides physical support for the osteoblastic cells against the implant surface and allows for automation. Thus, the amount of care required during the addition and removal of nutrient medium is reduced and a more uniform cell growth on the implant surface is achieved.

The following examples are offered by way of illustration and not for work limitation.

EXPERIMENTAL

EXAMPLE 1

Tissue and Cell Isolation

Bone-forming osteoblastic tissue is removed from the calvaria of an embryonic chick (between the ages of 12-17 gestation days) and freshly dissected with sterile surgical blades into fragments of less than about 1 mm³ (Gerstenfield, et al., *The Anatomical Record* (1990), 228, 93-103; Moore, et al., *Biochem.* (1991), 30, 2501-2508; Gotoh, et al., *Eur. J. Biochem.* (1990), 187, 49-58; Gotoh, et al., *Biochem. Biophys. Res. Commun.* (1990), 173, 471-479; Finer, et al., *J. Mol. Cell. Biol.* (1985), 5, 1415-1424; Ecarot-Charrier, et al., *Bone* (1988), 9, 147-154; Bhargava, et al., *Bone* (1988), 9, 155-163). Using sterilized solutions the tissue fragments are washed in phosphate buffer solution (PBS). Tissue fragments are then enzymatically treated in trypsin/collagenase (2%) for 2.5 hours to separate and isolate cells. The osteoblastic cells are then cold-filtered (0.45 μm at R.T.) to remove buffer solution and any non-osteoblastic components (Wong and Cohn, *Proc. Natl. Acad. Sci. USA* (1975), 72, 3167-3172). The cells are then washed and filtered repeatedly, generally 3-5 times, With fresh media over about 6 hours. The final filter-passage is carried out using a 0.2 μm filter. After dispersing the cells at $2.5 \times 10^5 - 5 \times 10^5$ cells/ml in phosphate buffer solution, the cell dispersion is centrifuged at 30° C. and the resulting cellular pellet dispersed in growth MEM media, 10% FBS. The cells are then grown for a period of 2-3 weeks in a petri dish at 37° C. with 5% $CO_2$ tension, the medium being changed every two days.

EXAMPLE 2

Gel Coating

Osteoblastic cells having a concentration of $2.5-3 \ 10^5$ cell/ml are placed in growth MEM medium, 10% FBS, 0.25% gelatin. After 2 hours, implants are dipped into the medium, with the only area contacted being where bony growth is desired. The procedure is carried out at ambient conditions. The implants are removed from the medium resulting in a thin layer (~0.1 mm) of the medium containing osteoblasts coated onto the implant. The implants are then placed into a 37° C., 5% $CO_2$ environment for a period of under 12 hours (usually at least 6 hours).

Figure 4A:
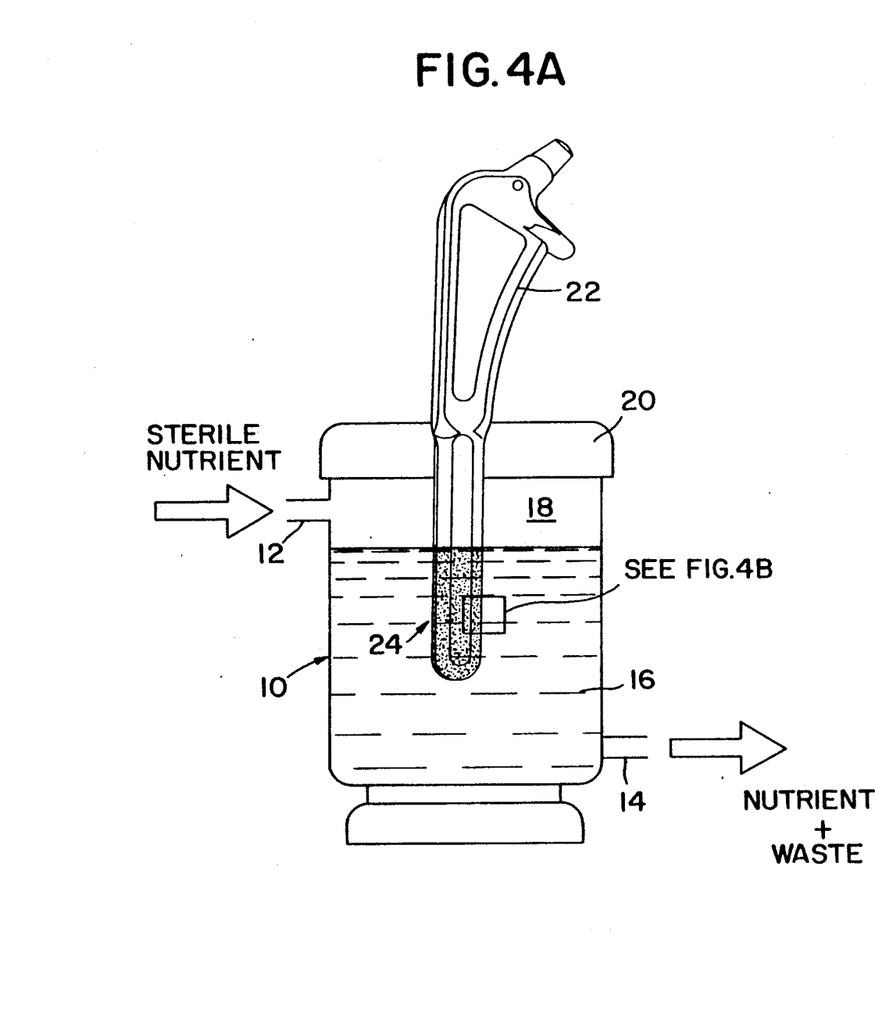
FIG. 4 is a diagrammatic view of the filter chamber employed to grow osteoblastic cells.
Figure 4B:
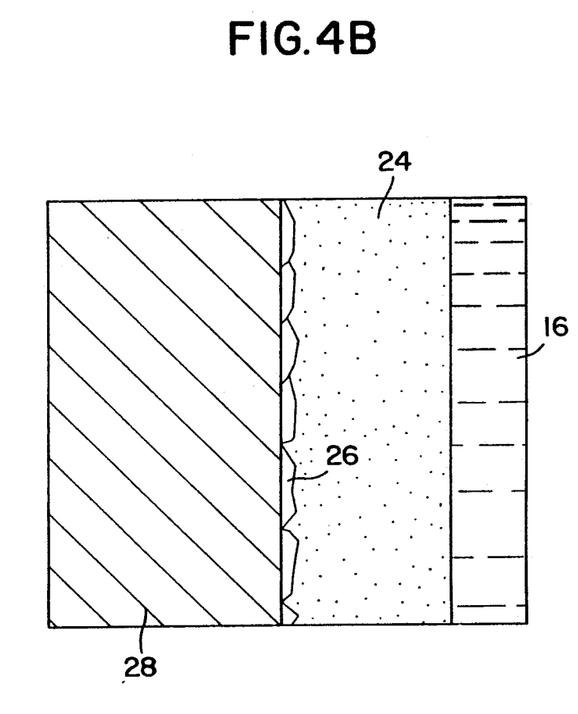
FIG. 4B is an enlarged view of a portion of the nutrient-immersed prosthesis coated with gel and cells.

The implants are then placed in a sterile chamber containing the medium MEM, 10% FBS, 1% gelatin (see FIGS. 4A and 4B). The implants were incubated for 31 days allowing for cellular multiplication on the implant surface with bony tissue formation; at 21 days growth media was changed to 0.1 M β-glycerol phosphate media, 0.025 mg/ml ascorbic acid, and were allowed to incubate an additional 10 days.

Figure 1:
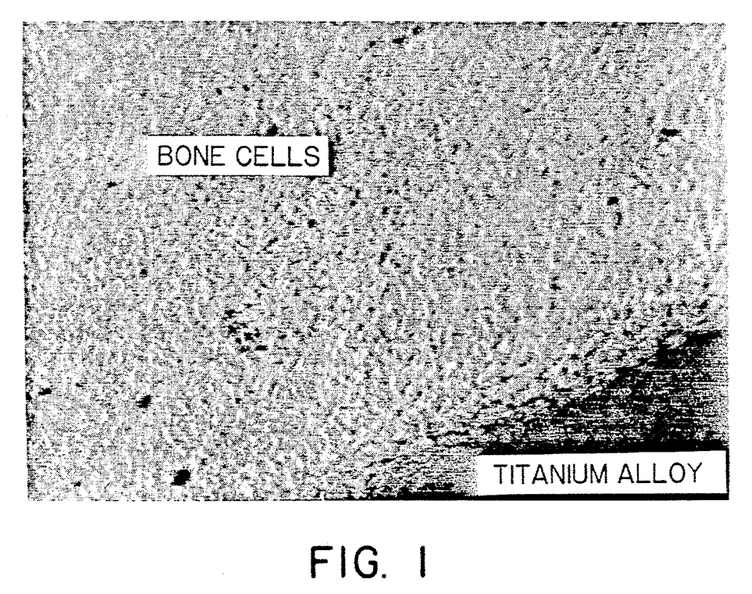
FIG. 1 is a photomicrograph from a phase-contrast light microscope showing the homogenous osteoblastic cell migration and growth along a titanium alloy surface.

The implant employed was made of titanium-alloy based metal. This implant was then subjected to various physical studies. In FIG. 1, a photomicrograph from a phase-contrast light microscope shows the homogeneous osteoblastic cell migrating and growing along the titanium alloy surface (Karnovsky, *Am. Soc. Cell Biol.* (1971), Abstract 284, New Orleans, p. 146). Newly-formed osteoblastic cells are growing homogeneously on the implant peripheral region.

Figure 2:
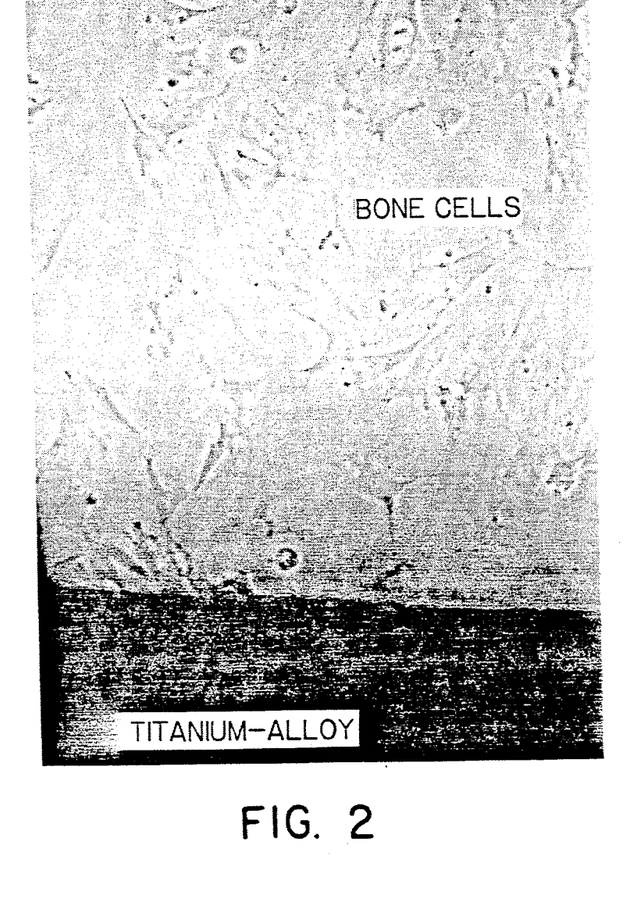
FIG. 2 shows the implant peripheral region at a higher magnification, with osteoblast cells displaying radial growth propagation along the surface of the prosthesis.

In FIG. 2, the implant peripheral region is shown at a higher magnification, with osteoblast cells displaying homogeneous outgrowth along the surface of the titanium alloy.

Figure 3:
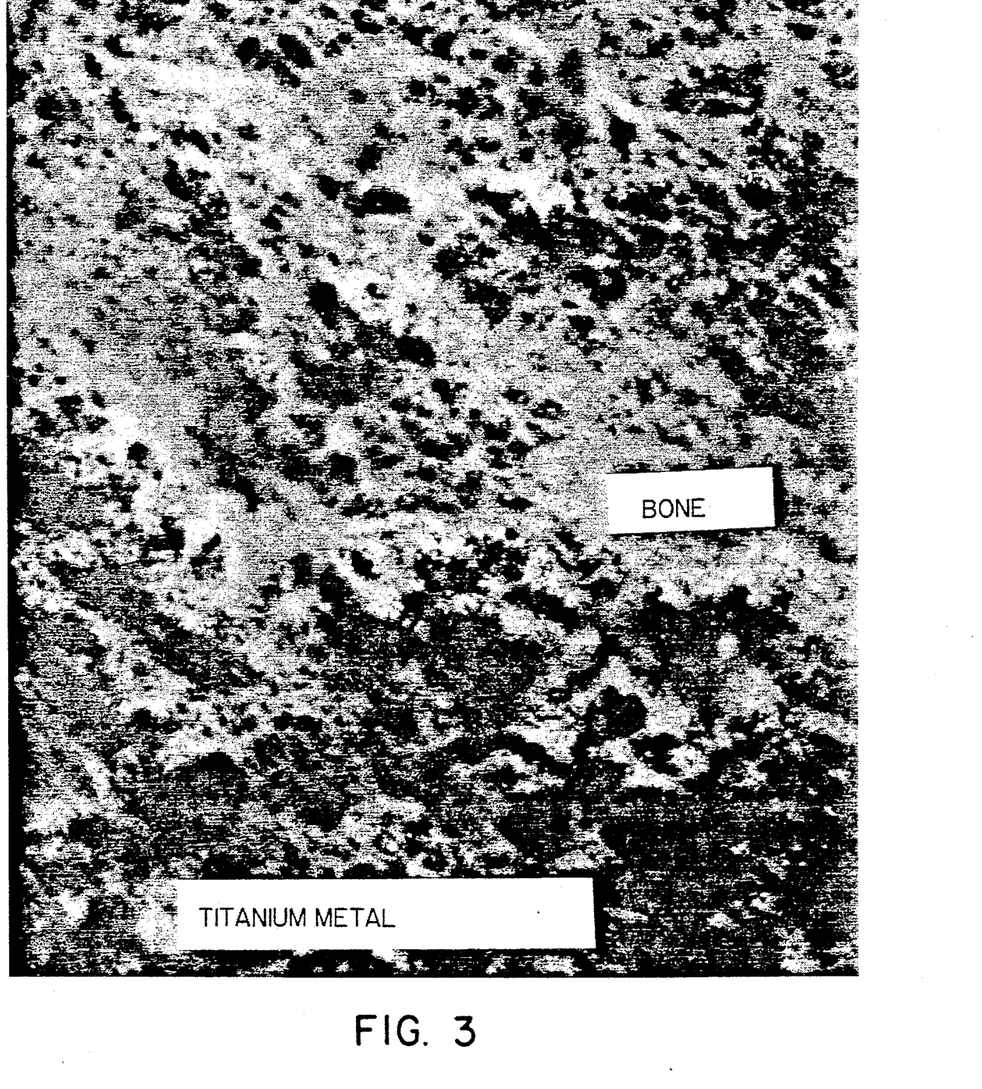
FIG. 3 illustrates the layers of calcium phosphate minerals on the surface of the implant.

In FIG. 3, newly formed layers of calcium phosphate minerals on the surface of the implant after 45 days of cell culture are illustrated.

In FIG. 4A the growth reactor 10 has an inlet 12 and a lower outlet 14 which allows for the flow of nutrient medium 16 through chamber 18. Cap and prosthesis holder 20 encloses the chamber 18 and supports prosthesis 22 which is partially immersed in nutrient media 16. The portion of prosthesis 22 immersed in nutrient media 16 and coated with gel 24 becomes coated with a bony structure by cells 26.

In the exploded view, (FIG. 4B) the prosthesis surface 28 is coated with cells 26 in gel 24 containing nutrient media.

Figure 5:
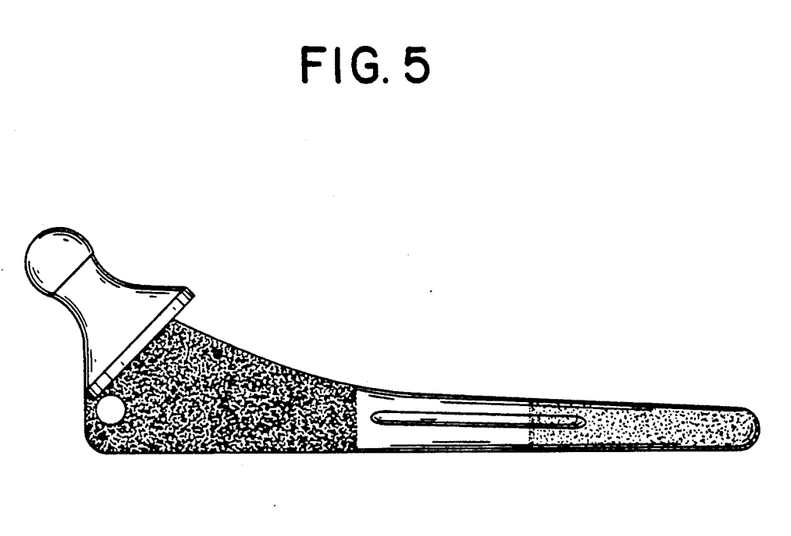
FIG. 5 is a photograph of the orthopedic implant coated with bone material (arrows) in accordance with the subject invention.

FIG. 5 shows a prosthesis with a bony structure coating.

It is evident from the above results, that bony tissue can be grown on the surface of devices of unnatural materials, such as prostheses. The tissue can provide for an acceptable border between the prosthesis and the natural tissue present in the patient into which the prosthesis is implanted. Thus, better bonding can be achieved between the prosthesis and the natural bone, so as to substantially reduce the incidence of failure. Various advantages may accrue by the subject procedure, which may allow for more rapid healing, improve support, and promote for longer-lasting more comfortable prosthesis.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An in vitro method for producing an implant device comprising a porous metal or metal alloy surface of said implant device coated with bony tissue as a result of laying down of said bony tissue by osteoblasts, said method comprising:

dispersing viable osteoblast cells in a gel medium comprising a nutrient medium;

coating said surface with said gel medium; and incubating said gel medium coated surface in a growth medium providing nutrients for the growth of said osteoblasts for sufficient time for said bony tissue to be laid down.

2. A method according to claim 1, wherein said osteoblasts are present in said gel medium in a sufficient number and concentration to coat said surface with a stable bony coating, said concentration is about $10^5$ to $10^6$ cells/75 cm$^2$.

3. A method according to claim 1, wherein said growth medium comprises serum.

4. A method according to claim 1, wherein said incubation comprises about 21 days in a first growth medium comprising serum and then an additional at least about 7 days wherein said medium comprises $\beta$-glycerol media and ascorbic acid.

5. A method according to claim 1, wherein said gel medium is at a thickness of about 0.05 to 1 mm.

6. A in vitro method for producing an implant device comprising a porous metal or metal alloy surface of said implant device coated with bony tissue as a result of laying down of said bony tissue by osteoblasts, said method comprising:

dispersing viable osteoblast containing tissue from a mammalian host in a physiological acceptable buffer solution;

transferring the osteoblasts into a gel medium comprising a nutrient medium;

coating said surface with said gel medium; and incubating said gel medium coated surface in a growth medium providing nutrients for the growth of said osteoblasts for sufficient time for said body tissue to be laid down, to provide a coated device to be introduced into said mammalian host.

* * * * *